(12) United States Patent
Müller

(10) Patent No.: US 6,233,305 B1
(45) Date of Patent: May 15, 2001

(54) METHOD, APPARATUS AND THEIR USE IN TOMOGRAPHIC IMAGING

(75) Inventor: Timo Müller, Espoo (FI)

(73) Assignee: Planmeca Oy (FI)

( * ) Notice: Subject to any disclaimer, the term of this patent is extended or adjusted under 35 U.S.C. 154(b) by 0 days.

(21) Appl. No.: 09/340,980

(22) Filed: Jun. 28, 1999

(30) Foreign Application Priority Data

Jun. 26, 1998 (FI) ......................................... 981476

(51) Int. Cl.⁷ ................................................. G01N 23/00
(52) U.S. Cl. ................................. 378/21; 378/10; 378/11; 378/22
(58) Field of Search .................. 378/21, 10, 11, 378/22

(56) References Cited

U.S. PATENT DOCUMENTS 4,669,103 * 5/1987 Barnes ................................... 378/10

* cited by examiner

*Primary Examiner*—David V. Bruce
*Assistant Examiner*—Pamela R. Hobden
(74) *Attorney, Agent, or Firm*—Steinberg & Raskin, P.C.

(57) ABSTRACT

A method of producing complex motion or spiral tomography images in tomographic imaging, comprising the steps of positioning an object to be imaged in a fixed position, arranging a radiation source on one side of the object to be imaged, arranging a detector on a second diametrically opposed side of the object to be imaged from the radiation source, the detector receiving radiation from the radiation source, while the radiation is being received, rotating the radiation source and the detector substantially around a vertical axis passing through the object to be imaged in a controlled manner whereby a tomographic effect is produced, while the radiation is being received, moving the radiation source in a first vertical direction, while the radiation is being received and simultaneously with the step of moving the radiation source, moving the detector in a second vertical direction opposite from the first vertical direction, and wherein the radiation source and the detector are moved independently from one another.

27 Claims, 5 Drawing Sheets

METHOD, APPARATUS AND THEIR USE IN TOMOGRAPHIC IMAGING

FIELD OF THE INVENTION

The present invention relates generally to a method, apparatus and their use for tomographic imaging and, more particularly, to a method and apparatus for producing complex motion or spiral tomography images in medical x-ray imaging.

BACKGROUND OF THE INVENTION

Imaging methods utilizing electromagnetic radiation can be divided into two groups: radioscopic methods and tomographic methods. In traditional radioscopy, the radiation source, the object to be imaged and the radiation detector, e.g., an x-ray film, are stationary with respect to one another during the imaging session. Imaging methods in which a narrow beam is moved over the object to be imaged are also known.

Tomographic methods can be divided into linear (i.e. planar) tomographic methods and complex motion or spiral tomographic methods. In linear tomographic imaging, the radiation source and the radiation detector are moved with respect to one another in a controlled manner. That is, the radiation source and the radiation detector are rotated around a vertical axis passing through the object to be imaged so that the radiation beam from the radiation source passes through the object to be imaged and is received by the detector, the radiation beam remaining in a single plane. In complex motion tomography, in addition to rotating around the vertical axis passing through the object to be imaged, the radiation source and radiation detector move vertically in opposite directions from one another thereby varying the angle of the radiation beam passing through the object to be imaged. Both methods preferably use a beam which is of the same size as the object to be imaged. Therefore, in complex tomography, the object to be imaged is usually held in place as the radiation source and radiation detector move dependently on one another on opposite sides of the object to be imaged in opposite vertical directions so that the beam penetrates the object at different angles. However, the location at which the beam penetrates the object does not change. These methods provide accurate images of the imaging area in the center of rotation of the beam, whereas the other parts of the object are blurred partially or totally.

There also exist "narrow beam tomography" methods in which a beam considerably narrower than the object to be imaged sweeps across the area to be imaged and the beam is turned with respect to the object to be imaged. In that case, the imaging means (i.e., the radiation source and the radiation detector) must be moved in a controlled manner so that the detector moves in relation to the beam at a lateral velocity which corresponds to the perpendicular sweeping speed of the beam in the area to be imaged multiplied by the ratio of magnification, i.e., by a coefficient which is the ratio of the distance of the beam focus (radiation source) and the distance of the focus from the area to be imaged. Here, the term "detector" refers to a film or the like. In digital imaging, for example, the movement of the detector with respect to the area to be imaged may be replaced with a suitable electrical function, such as a charge transfer on the surface of a semiconductor sensor.

Thus, it is known to move the radiation source and the radiation detector both horizontally and vertically for producing a tomographic effect. Many prior art devices that enable complex motion paths have very massive structures, and thus it may not be possible to move the imaging means rapidly and change its direction due to the limits set by the general physical principles of moving heavy masses and mechanical solutions of the devices. Against this background, it is not easy to develop commercially feasible devices. The present trend is to develop devices which enable the use of the same device for various purposes, i.e., the goal is to be able to use the same device in different tomographic methods and for imaging different projections. When the same device has different imaging modes, investment in imaging sensors based on modem digital technology becomes more profitable, which lowers the threshold of introducing them. Digital technology facilitates a doctors' work since, for example, it not only allows doctors to produce better images than earlier thereby enabling them to make more accurate diagnoses, but it also enables doctors to store the images and manage them in electronic form, together with all of the other documents related to the patient.

OBJECTS AND SUMMARY OF THE INVENTION

An object of the present invention is to provide a new device for complex tomographic imaging which uses prior devices intended for linear tomographic imaging. For example, several prior art devices used for linear x-ray photography of the cranial area already include structures which can be utilized as such or with minor structural or programmatical changes for complex motion tomographic imaging.

Prior art tomographic imaging devices include a device such as that disclosed in Finnish Patent 88671, in which the radiation source and radiation detector (sometimes referred to herein collectively as "imaging means") of the device are attached to respective ends of a suspension arm that can be rotated in the horizontal plane, the arm being provided with a degree of freedom for moving in the direction of the axis between the imaging means. Furthermore, the arm can be tilted with respect to the horizontal plane. The imaging means can also be arranged so that they can be moved vertically with respect to the object to be imaged by forming the suspension arm in the shape of an arc and by moving the arm in the direction of its longitudinal axis along a supporting structure in which the imaging means move upwards along a curved path of the arm and correspondingly downwards on the opposite sides of the object to be imaged. The publication does not disclose use of these features (which is known per se from other contexts) for actual complex motion or spiral tomography imaging, i.e., the use of the upward movements enables the production of a tomographic effect with respect to two directions during radiation. The device according to the Finnish publication utilizes a narrow beam, and the imaging means are moved vertically with respect to the object to be imaged in order to obtain a perpendicular cross-sectional image of the patient's teeth which are diagonal to the vertical plane.

In tomographic imaging, it is particularly important that the object to be imaged and the imaging means are in a controlled position with respect to each other during the entire imaging session. There are several prior art patents wherein the object is to position the object to be imaged and/or the imaging means accurately before imaging. Examples of mechanical and motorized positioning are disclosed in U.S. Pat. Nos. 5,666,392 and 5,642,392. However, these solutions are related to controlled and reproducible positioning of the object to be imaged and/or the imaging means before the actual imaging or between separate radiation sessions, such as in tomosynthesis imaging. The patents do not disclose devices for controlling the movement of the imaging means during radiation when the tomographic movement is performed in complex motion tomographic imaging. The tomographic movement is usually implemented so that it is continuous, but in some cases it may be necessary to stop the movement and/or radiation momentarily for purely technical reasons.

The present invention combines the ideas of utilizing structures that already exist in imaging devices for producing a tomographic effect by means of a vertical movement and producing a vertical movement without having to move large masses which imposes limitations on tomographic imaging. The method of implementing the tomographic movement includes the feature of synchronizing, by means other than conventional mechanical synchronization, the vertical movement of the imaging means with respect to the object to be imaged. For example, according to one preferred embodiment of the invention, the imaging means, i.e., the radiation source and the radiation detector, are provided with means for moving the radiation source in the vertical direction using the means which control the height of the imaging equipment with respect to the object to be imaged, such means already being included in devices of this kind for other reasons. Therefore, in that embodiment, it is sufficient to provide only one of the imaging means, i.e., the radiation detector, with a structure for implementing the vertical counter-movement. Thus, the structures which already exist in prior art devices can be utilized.

BRIEF DESCRIPTION OF THE DRAWINGS

A more complete appreciation of the present invention and many of the attendant advantages thereof will be readily understood by reference to the following detailed description when considered in connection with the accompanying drawings in which.

DETAILED DESCRIPTION OF THE INVENTION

Figure 1:
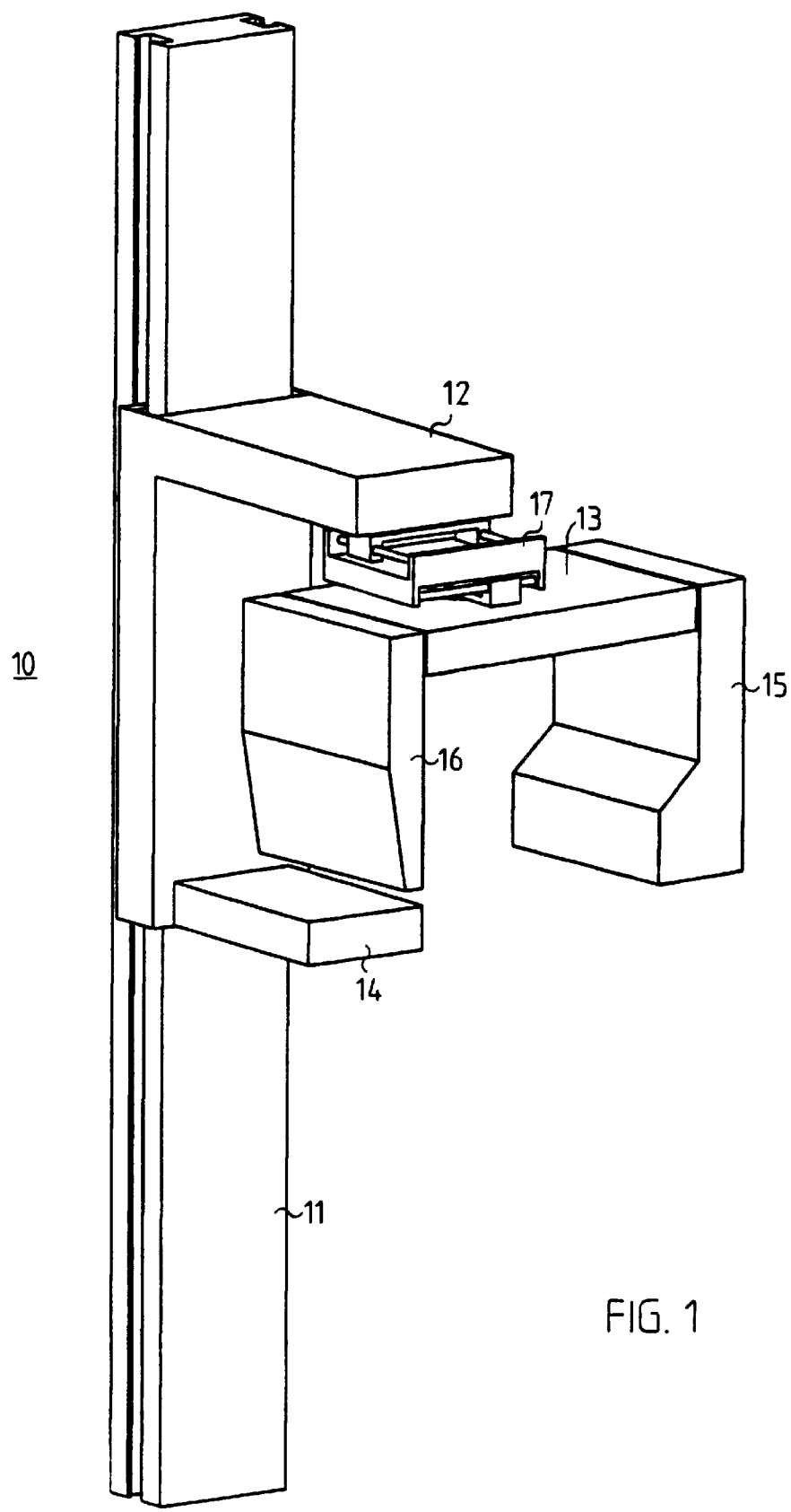
FIG. 1 shows a typical prior art apparatus used for imaging teeth and the cranial area.
Figure 2:
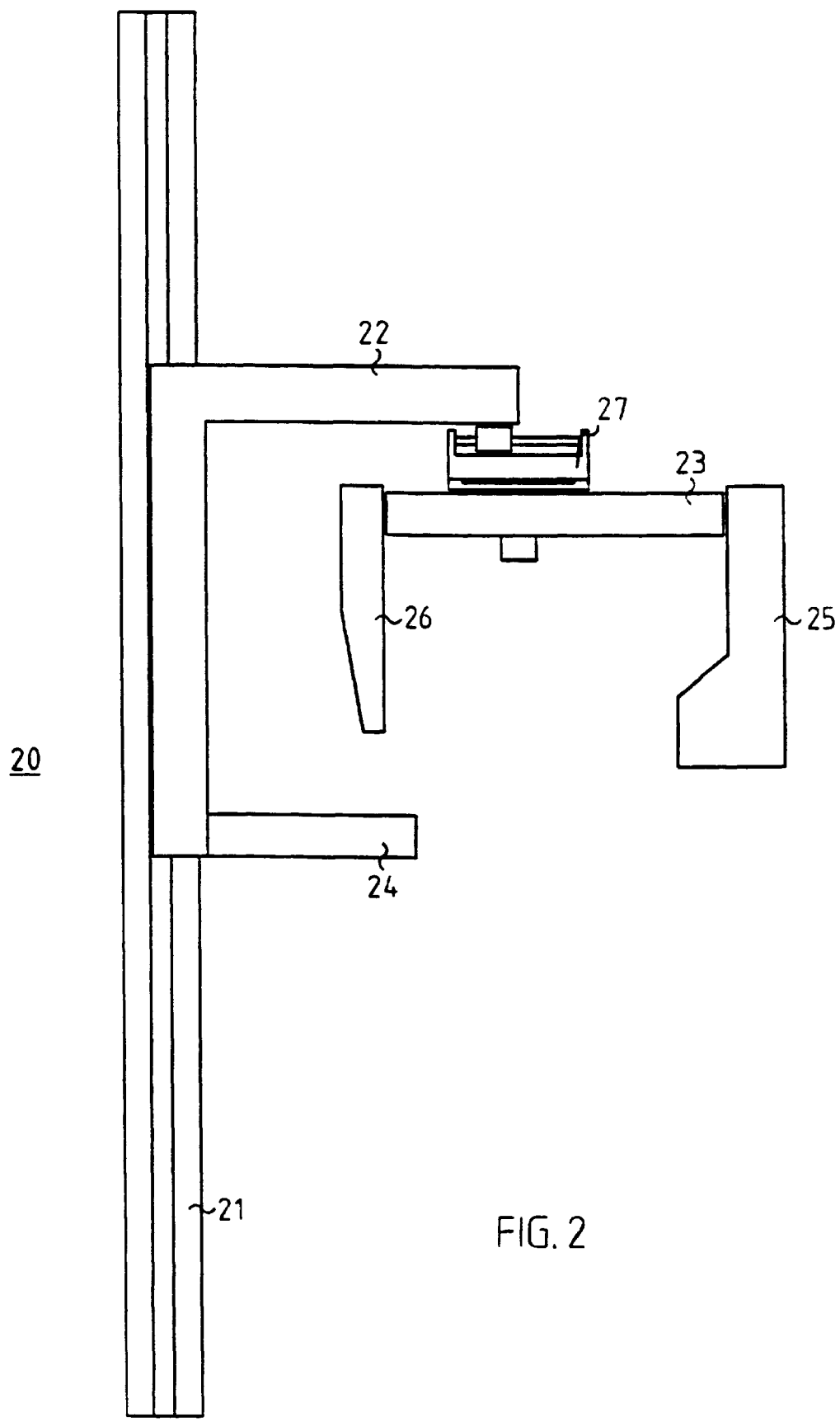
FIG. 2 is a side view of the prior art apparatus shown in FIG. 1.

Referring now to the drawings wherein like reference characters designate identical or corresponding features throughout the several views, and more particularly to FIGS. 1 and 2, a typical prior art apparatus 10, 20 for imaging the teeth and the cranial area is provided which, in accordance with the invention, can also be used for complex motion tomographic imaging with relatively small changes. The apparatus 10, 20 consists of a first frame part 11, 21, a second frame part 12, 22 slidably connected to the first frame part 11, 21 and a third frame part 13, 23 coupled to the second frame part 12, 22. The first frame part 11, 21 may be attached to the floor or wall, in which case it comprises means for altering the height of the second frame part 12, 22. Alternatively, the second frame part 12, 22 may be fixed to the first frame part 11, 21, in which case the first frame part 11, 21 comprises means for adjusting the length thereof (e.g. a telescopic structure). The third frame part 13, 23 functions as a suspension arm of a radiation source 15, 25 and a detector 16, 26 (collectively, the imaging means), which are attached to opposing ends of the suspension arm. The third frame part is coupled to the second frame part via fixing and moving means 17, 27. Means for positioning the object to be imaged (not shown) may be arranged in association with a fourth frame part 14, 24. The fourth frame part may also comprise a control panel (not shown) of the apparatus.

For sake of clarity, the second and third frame parts will sometimes be referred to herein collectively as "imaging equipment", the radiation source and the radiation detector will sometimes be referred to herein collectively as "imaging means", and the third frame part will sometimes be referred to herein as the "suspension arm."

In some prior art devices, the fixing and moving means 17, 27 which couple the second frame part 12, 22 to the third frame part 13, 23, i.e. the suspension arm of the imaging means, allow the suspension arm 23 to rotate and move in the horizontal plane in the x and y directions. The device often comprises a control system for controlling the movements of the suspension arm 13, 23, which may be implemented by means of computer-controlled electric motors and guide tracks provided in the fixing and moving means 17, 27 of the suspension arm. The structures that move the suspension arm can be implemented in various ways. Most typically, in apparatuses of this kind, the suspension arm is able to both move in the horizontal plane to a desired location so that the object to be imaged is positioned between the radiation source and the radiation detector and rotate around a fixed axis with respect to the object to be imaged. In addition, if a film or the like is used as the detector 16, 26, the prior art apparatuses often also include means for moving the film horizontally.

Figure 3B:
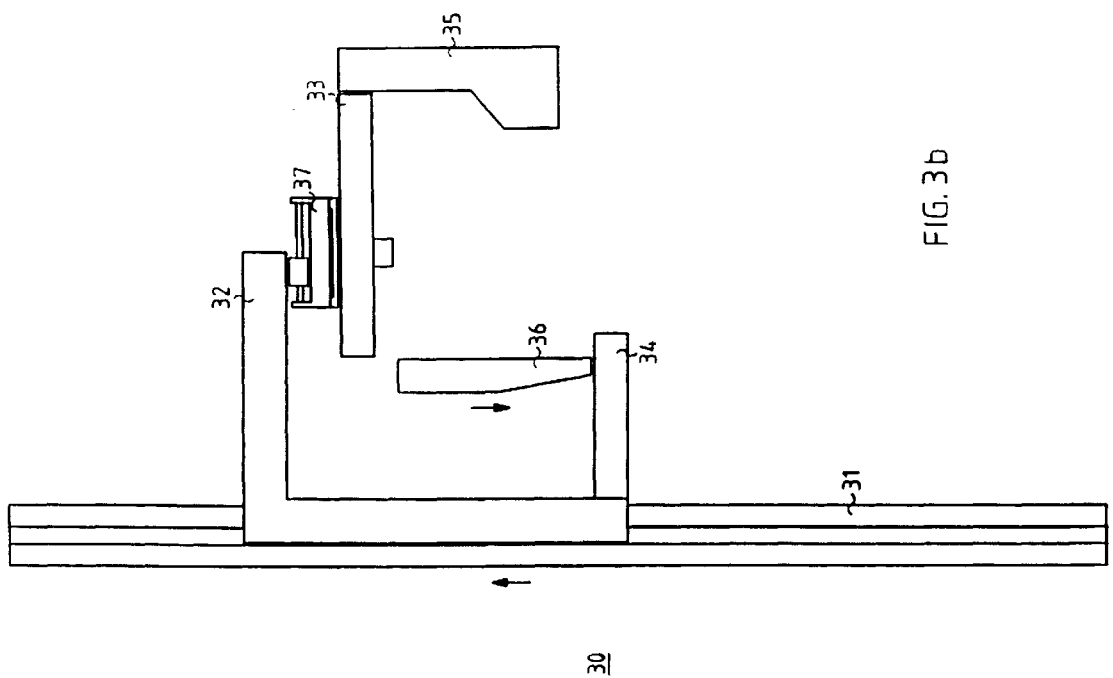
FIGS. 3a and 3b show one embodiment of the invention in which the prior art apparatus of FIG. 1 is modified so that it can also be used for complex motion tomographic imaging.
Figure 3A:
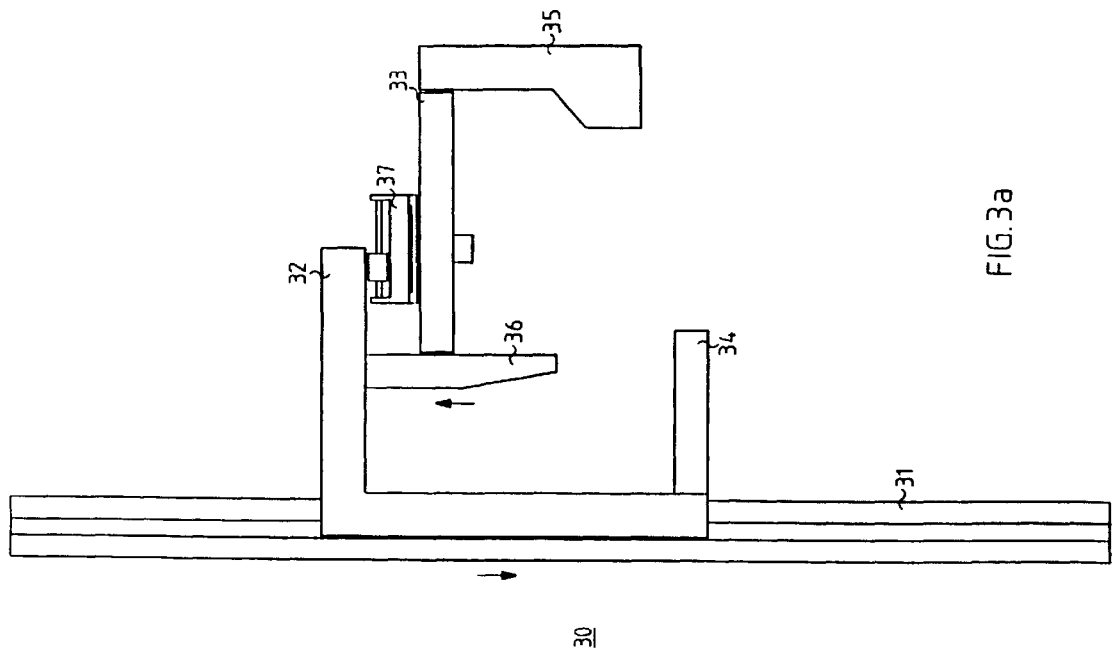

FIGS. 3a and 3b show a first embodiment of the present invention in which the prior art apparatus shown in FIG. 1 has been modified in accordance with the invention. In this embodiment, means for moving the detector 36 vertically are provided. The means for moving the detector 36 in a vertical direction can be any means known in the art for moving a film or the like in a vertical direction. The direction of movement of the detector 36 is depicted by arrow A. By providing the detector 36 with the ability to move vertically, the apparatus of the invention can be used for producing complex motion tomographic images. That is, complex motion tomographic images can be produced by implementing the vertical tomographic movement of the detector 36 along with its counter-movement with respect to the object to be imaged, the counter-movement being provided by altering the height of the second frame part 32 in one direction (arrow B) and by moving the detector 36 in the other direction. The detector 36 and the second frame part 32 are arranged so that they move independently of one another. That is, their movement with respect to one another is accomplished without mechanical synchronization, i.e., by controlling their movement using separate motors. While motors are used in the preferred embodiment, any known means for moving the detector 36 and the second frame part 32 can be used such as manual cranks. In other embodiments of the invention, the counter-movement can be implemented in a manner not shown. For example, the radiation source 35, rather than the detector 36, can be moved vertically in the opposite direction from the movement of the second frame part 32.

Figure 4B:
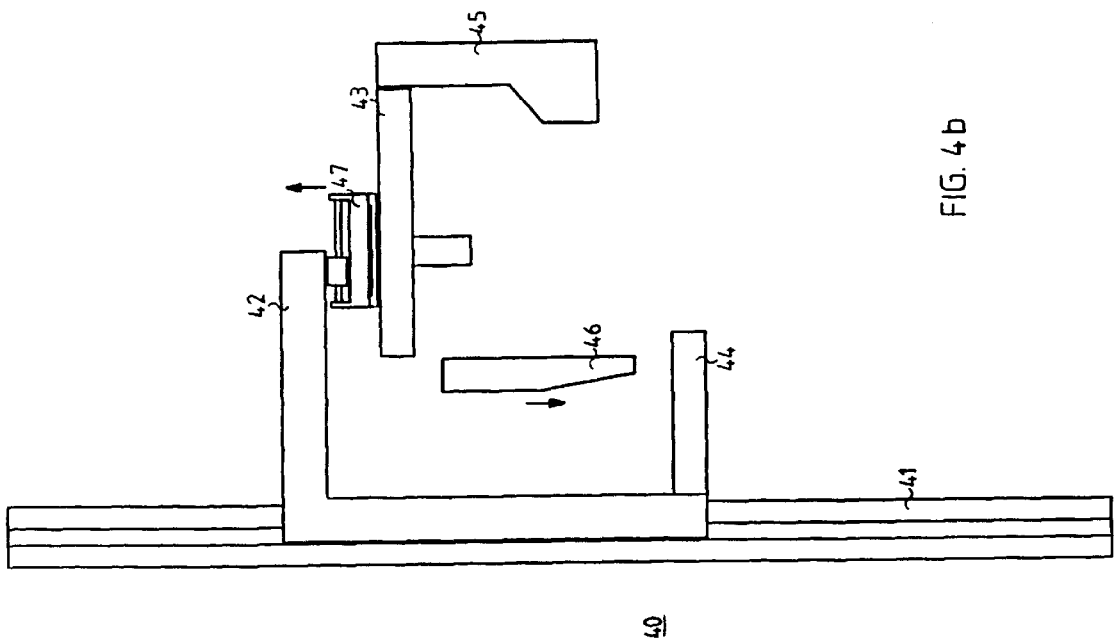
FIGS. 4a and 4b show a second embodiment of the invention in which the prior art apparatus of FIG. 1 is modified so that it can also be used for complex motion tomographic imaging.
Figure 4A:
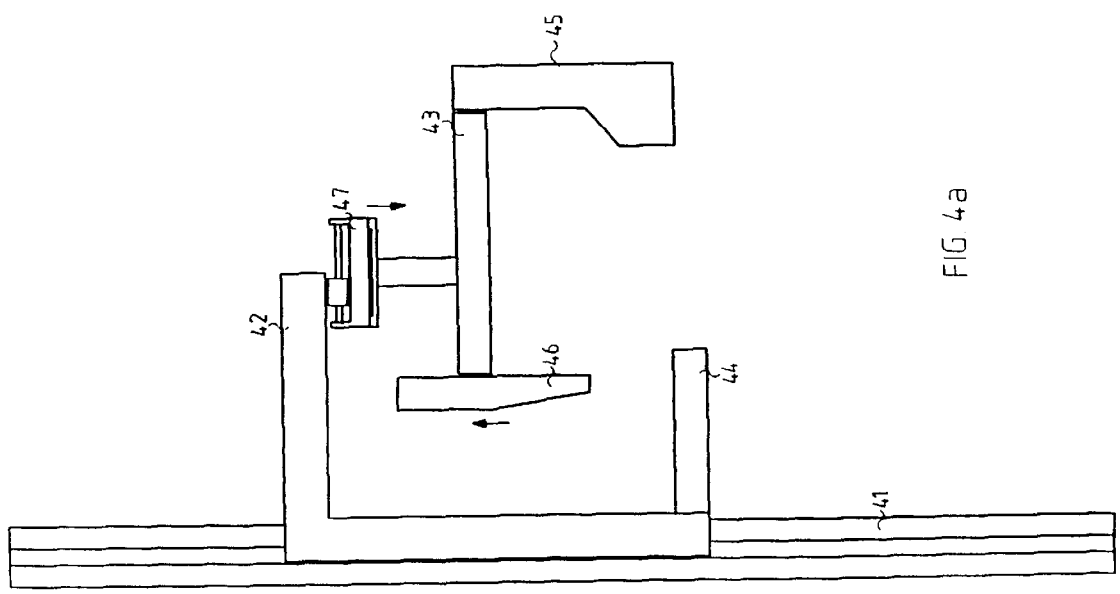

Another embodiment of the present invention is shown in FIGS. 4a and 4b. In this embodiment, rather than adjusting the vertical position of the radiation source via the second frame part, means for moving the third frame part 43 in the vertical direction (arrow C) are provided. The means for moving the third frame part 43 can be any conventional means such as a motorized rack and pinion arrangement. As stated with respect to the previous embodiment, the means for moving the third frame part 43 and the means for moving the detector 46 are independent from one another. That is, in one embodiment, separate motors act as the moving means for the third frame part 43 and the detector 46, respectively.

Figure 5B:
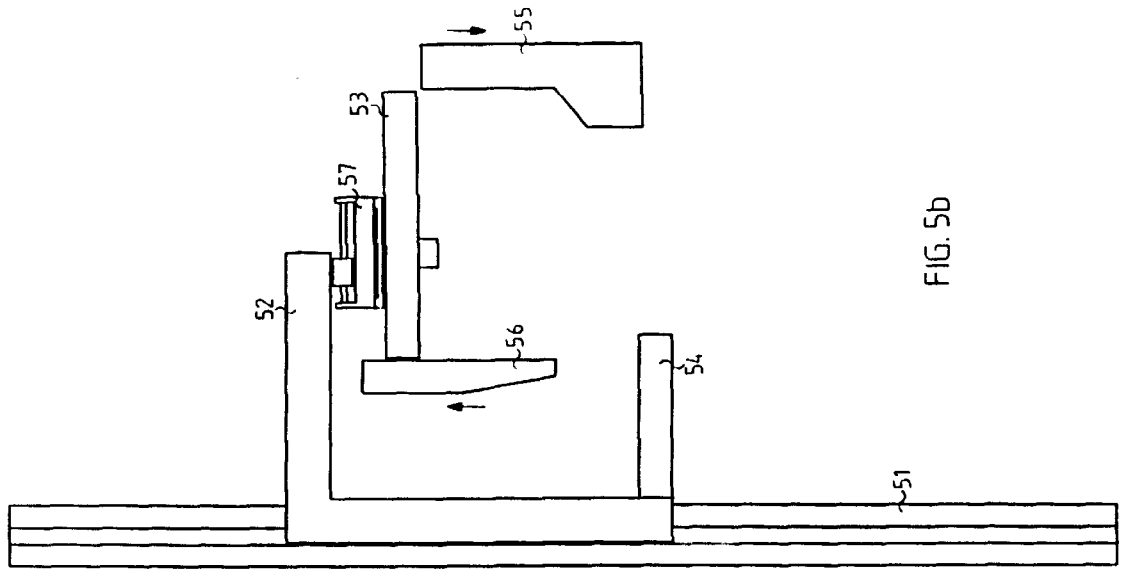
FIGS. 5a and 5b show a third embodiment of the invention in which the prior art apparatus of FIG. 1 is modified so that it can also be used for complex motion tomographic imaging.
Figure 5A:
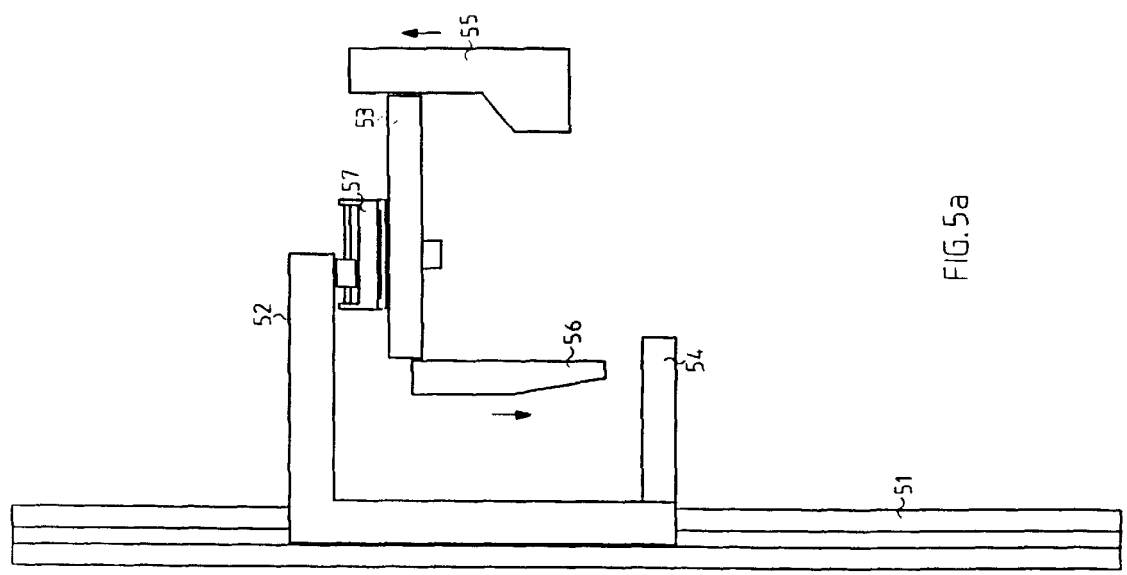

A third embodiment of the present invention is shown in FIGS. 5a and 5b. In this embodiment, each component of the imaging means, i.e. each of the radiation source 55 and the detector 56, are provided with means for moving in the vertical direction. The movement of radiation source 55 is depicted by arrow D. Any conventional means for moving these devices can be utilized. However, separate motors are preferably used which act independently from one another.

In each of the above embodiments, a prior art linear tomographic image device is modified so that complex tomographic images are able to be produced in addition to linear tomographic images. Such is accomplished by providing means for moving the detector and the radiation source vertically in opposite directions while both are being rotated about the object to be imaged so that the radiation beam travels from the radiation source to the detector, through the object to be imaged, at various angles. This is in contrast to linear tomography where the radiation detector and radiation source are rotated around the object to be imaged in a controlled manner while the center of rotation of the radiation beam remains in one place.

Each of the different embodiments of the present invention discussed above has its pros and cons with respect to the other embodiments. In the embodiment shown in FIGS. 3a and 3b, the prior art apparatuses need only be provided with one new means for movement. On the other hand, in the embodiments shown in FIGS. 4a and 4b, it is not necessary to move as large masses as in the embodiments of FIGS. 3a and 3b to produce the second vertical movement. However, few prior art apparatuses are provided having means for moving the suspension arm 43 in the vertical direction.

In the embodiments shown in FIGS. 5a and 5b, the masses that must be moved are smaller than in the other embodiments of the invention. However, many prior art apparatuses must be provided with new mechanics before the second vertical movements can be implemented in practice.

The present invention is preferably used for producing longitudinal or cross-sectional x-ray images of individual sections of the dental arc. In this case, considering the patient's positioning, the apparatus would often be used in the position described in FIGS. 3 and 4. With regard to space utilization, it is preferable to move the radiation source rather than the detector. However, the radiation source is typically heavier than the detector so that it is preferable to move of the detector.

In the present invention, a beam which is of the same size as the object to be imaged is preferably used. However, it is possible to utilize a beam which is narrower than the object to be imaged, i.e., to use narrow beam tomography. In that case, however, the imaging process is relatively slow, which imposes practical limitations on this application of the invention.

Obviously, numerous modifications and variations of the present invention are possible in light of the teachings hereof. For example, the embodiments of the invention described herein illustrate applications of the invention mainly by means of devices known from odontological X-ray photography. Even though the invention is particularly suitable for developing solutions known from odontological X-ray photography of the cranial area, its applicability is not limited only to the embodiments described by the examples. Therefore, it is to be understood that the invention can be varied from the detailed description above within the scope of the claims appended hereto.

I claim:

1. A method of producing complex motion or spiral tomography images in tomographic imaging using an imaging apparatus, comprising the steps of:

positioning an object to be imaged in a fixed position;

arranging a radiation source on one side of the object to be imaged;

arranging a detector on a second diametrically opposed side of the object to be imaged from the radiation source;

the detector receiving radiation from the radiation source;

while the radiation is being received, rotating the radiation source and the detector substantially around a vertical axis passing through the object to be imaged in a controlled manner whereby a tomographic effect is produced;

while the radiation is being received, moving the radiation source in a first vertical direction;

while the radiation is being received and simultaneously with the step of moving the radiation source, moving the detector in a second vertical direction opposite from the first vertical direction; and wherein the radiation source and the detector are moved mechanically independently from one another.

2. The method as in claim 1, wherein the radiation source and the detector are moved by means of separate motors.

3. The method as in claim 1, wherein the radiation source is moved by means of its own motor and the detector is moved by means of a motor which also moves another part of the imaging apparatus.

4. The method as in claim 3, wherein the detector is moved by means which adjust the height of the detector and radiation source with respect to the object to be imaged.

5. The method as in claim 3, further comprising the step of coupling the detector and the radiation source to a suspension arm, and wherein the detector is moved by means which adjust the height of the suspension arm.

6. The method as in claim 1, wherein the detector is moved by means of its own motor and the radiation source is moved by means of a motor which also moves another part of the imaging apparatus.

7. The method according to claim 6, wherein the radiation source is moved by means which adjust the height of the detector and radiation source with respect to the object to be imaged.

8. The method as in claim 6, further comprising the step of:

coupling the detector and the radiation source to a suspension arm, and wherein the radiation source is moved by means which adjust the height of the suspension arm.

9. The method as in claim 1, further comprising the step of narrowing the width of the radiation received from the radiation source to be narrower than the width of the object to be imaged.

10. The method as in claim 1, wherein the radiation is X-radiation.

11. An apparatus for producing complex motion and spiral tomography images of an object to be imaged which is positioned in a fixed position, comprising:

a radiation source arranged on one side of the object to be imaged structured and arranged to generate an electromagnetic beam;

a radiation detector arranged on a second diametrically opposed side of the object to be imaged from said radiation source, said radiation detector being structured and arranged to receive said electromagnetic beam;

means for rotating said radiation source and said radiation detector substantially around a vertical axis passing through the object to be imaged in a controlled manner whereby a tomographic effect is produced;

means for moving said radiation source in a first vertical direction; and means for moving said detector independently from said radiation source in a second vertical direction opposite from said first vertical direction.

12. The apparatus according to claim 11, wherein said means for moving said radiation source and said means for moving said detector each comprise a separate motor, each of said motors being structured and arranged to move only a respective one of the radiation source and the detector.

13. The apparatus as in claim 11, further comprising:

a first frame part;

a second frame part slidably coupled to said first frame part;

a third frame part coupled to said second frame part;

wherein said radiation source and said detector are coupled to opposing ends of said third frame part; and wherein said means for moving said radiation source comprise a separate motor for moving only said radiation source and wherein said means for moving said detector comprise means for moving another part of the apparatus.

14. The apparatus as in claim 13, wherein said means which move said other part of the apparatus comprise means which adjust the height of said second frame part and said third frame part with respect to said object to be imaged.

15. The apparatus as in claim 13, wherein said means which move said other part of the apparatus comprise means which adjust the height of said third frame part with respect to the apparatus.

16. The apparatus as in claim 11, further comprising:

a first frame part;

a second frame part slidably coupled to said first frame part;

a third frame part coupled to said second frame part;

wherein said radiation source and said detector are coupled to opposing ends of said third frame part; and wherein said means for moving said detector comprise a separate motor for moving only said detector and wherein said means for moving said radiation source comprise means for moving another part of the apparatus.

17. The apparatus as in claim 16, wherein said means which move said other part of the apparatus comprise means which adjust the height of said second frame part and said third frame part with respect to said object to be imaged.

18. The apparatus as in claim 16, wherein said means which move said other part of the apparatus comprise means which adjust the height of said third frame part with respect to the apparatus.

19. The apparatus as in claim 11, further comprising:

a first frame part for attaching the apparatus to the floor, a wall or to another supporting structure;

a second frame part movably coupled to said first frame part such that it can move in the vertical direction with respect to said first frame part; and a third frame part coupled to said second frame part, said radiation source and said radiation detector being coupled to said third frame part.

20. The apparatus as in claim 19, wherein said radiation source and said radiation detector are coupled to opposing ends of said third frame part; and said means for rotating said radiation source and said detector whereby a tomographic effect is produced comprise means for rotating said third frame part around a fixed point with respect to the object to be imaged.

21. The apparatus as in claim 20, wherein said third frame part is located in a horizontal plane and wherein the apparatus further comprises means for coupling said third frame part to said second frame part and for moving said third frame part in said horizontal plane with respect to said second frame part.

22. The apparatus as in claim 11, wherein said electromagnetic beam is narrower than said object to be imaged.

23. The apparatus as in claim 11, wherein said radiation source is an x-ray tube.

24. The apparatus as in claim 11, wherein said object to be imaged is the cranial area.

25. A method for modifying an apparatus for producing linear tomography images of an object to be imaged which is positioned in a fixed position, comprising a radiation source arranged on one side of the object to be imaged structured and arranged to generate an electromagnetic beam, a radiation detector arranged on a second diametrically opposed side of the object to be imaged from said radiation source, said radiation detector being structured and arranged to receive said electromagnetic beam, and means for rotating said radiation source and said radiation detector substantially around a vertical axis passing through the object to be imaged in a controlled manner whereby a tomographic effect is produced, comprising the steps of providing:

means for moving said radiation source in a first vertical direction; and means for moving said detector independently from said radiatoin source in a second vertical direction opposite from said first vertical direction.

26. The use of the method as in claim 1 for longitudinal or cross-sectional imaging of the cranial area, particularly for imaging of individual sections of the dental arc.

27. The use of the apparatus as in claim 11 for longitudinal or cross-sectional imaging of the cranial area, particularly for imaging of individual sections of the dental arc.

* * * * *